United States Patent
Fan et al.

(10) Patent No.: US 7,192,574 B2
(45) Date of Patent: Mar. 20, 2007

(54) STABLE COSMETIC SPRAYABLE PRODUCTS WITH A DESIRABLE NARROW CONICAL SPRAY PATTERN

(75) Inventors: Shimei Fan, Inverness, IL (US); Tirucherai V Vasudevan, Lake Zurich, IL (US)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 474 days.

(21) Appl. No.: 10/256,423

(22) Filed: Sep. 27, 2002

(65) Prior Publication Data

US 2004/0062740 A1    Apr. 1, 2004

(51) Int. Cl.
*A61Q 5/12*    (2006.01)
(52) U.S. Cl. .............................. 424/70.28; 424/70.11; 424/70.12
(58) Field of Classification Search ............... 424/70.1
See application file for complete search history.

(56) References Cited

U.S. PATENT DOCUMENTS

| | | | |
|---|---|---|---|
| 4,192,862 A | | 3/1980 | Pengilly |
| 5,720,964 A | * | 2/1998 | Murray ........................ 424/401 |
| 6,106,814 A | | 8/2000 | Raney et al. |
| 6,540,989 B2 | * | 4/2003 | Janchitraponvej .......... 424/70.1 |

FOREIGN PATENT DOCUMENTS

| | | |
|---|---|---|
| EP | 0 473 349 A | 4/1992 |
| WO | 95/20939 | 8/1995 |
| WO | 99/39684 | 8/1999 |
| WO | 01/08654 A1 | 2/2001 |
| WO | 01/91707 A | 12/2001 |

OTHER PUBLICATIONS

International Search Report Application No. PCT/EP 03/08767 mailed Nov. 25, 2003.
Chemical Abstracts No. XP-002261124 & JP 2002 104934 A, assigned to Kao Corp., "Hair Preparations Containing Polyoxyalkylenes and Polysiloxanes".
Patent Abstracts of Japan. vol. 01, No. 361 (C-459), & JP 62 132812 A assigned to Sunstar Inc.
JP 10/23538 (Oct. 1998) JP abstract.

* cited by examiner

*Primary Examiner*—Jyothsna Venkat
(74) *Attorney, Agent, or Firm*—Karen E. Klumas

(57) ABSTRACT

An aqueous leave-on hair conditioning composition which comprises:
a.) about 0.01 percent to about 10.0 percent of a quaternary ammonium compound;
b.) about 0.0 percent to about 10.0 percent of a silicone oil;
c.) about 0.00001 to about 0.05% of a polyoxyethylene polymer; and
d.) about 0.01 to 10% of a non-ionic surfactant
wherein said composition is substantially free of hair hold enhancing agents and which is substantially free of cationic cellulosic resins containing tetra-substituted nitrogen moieties,
is described.

14 Claims, No Drawings

STABLE COSMETIC SPRAYABLE PRODUCTS WITH A DESIRABLE NARROW CONICAL SPRAY PATTERN

BACKGROUND OF THE INVENTION

Compositions that can be used to condition hair are well known. Hair conditioning compositions are intended to leave hair manageable, soft, and shiny. Manageability is manifested as ease of combing in the wet and dry states, as well as preventing hair "fly-away" in the dry state. Most hair conditioning compositions are applied to hair when wet, usually as an after-treatment following the shampooing process. More recently, two-in-one conditioning shampoos have been developed which provide cleansing and conditioning of the hair with a single composition. Both two-in-one shampoos and after-treatment conditioners are usually rinsed off after being allowed to remain in contact with the hair for a brief period of time, and hence, are referred to in the art as "rinse off" type compositions. While the hair conditioning compositions of the present invention may be used as a rinse-off product, they are particularly intended to be "leave-on" product, that is, one which is applied to the hair in either wet or dry state, and is not subsequently rinsed off. Such leave-on products are typically applied to the hair from a pump-type spray dispenser in a form ranging from mist to a conical spray and finally to a jet stream. The most desirable spray pattern, from the point of view of product efficacy, is a conical spray pattern.

Although leave-on conditioners can be clear, homogeneous (single-phase) products, more efficacious conditioners typically are emulsions (two-phase) comprising a dispersion of conditioning agents such as quaternary ammonium compounds with or without fatty alcohols and volatile/non-volatile silicones suspended in an aqueous medium. Therefore, to maintain the efficacy of these products over a period of time the compositions should be physically stable, that is, no phase separation of the dispersed and the continuous phases should occur. Additionally, the composition should have a viscosity low enough to permit its application from a spray dispenser in a conical spray pattern.

Accordingly, one object of the present invention is to provide a conditioning composition that is in the form of physically stable emulsion.

Another object of the present invention is to provide an emulsion that can be sprayed from a pump dispenser having a conical spray pattern.

In the present invention, it has been surprisingly found that combining a non-ionic surfactant with a non-ionic polymer can provide both enhanced physical stability and a conical spray pattern to a dispersion containing a cationic conditioning surfactant and a silicone conditioning compound.

Patents and patent applications which are related to the field of the invention are as follows:

WO 99/39684 discloses a hair conditioning or detangling compositions, which could be a sprayable product, comprising a dispersion of cationic conditioning compound and a silicone compound suspended in an aqueous medium and optionally comprising components such as glycols or polyols, surfactants and fatty alcohols.

U.S. Pat. No. 4,192,862 discloses a hairspray product having improved hair-holding properties. The hairspray composition comprises, as is usual, a solution of a hairspray resin in a suitable solvent, but to improve the holding power there is also included a minor amount of a drag reducing agent which is soluble in the solvent for the hairspray resin. The drag reducing agent is present in an amount such that the weight ratio of the hairspray resin to the drag reducing agent is 10,000 to 2:1. The drag reducing agent amounts to less than 0.3% by weight of the composition.

JP 10235238 discloses an aerosol container for a hair care cosmetic which has an injection nozzle and which develops a conical spray pattern of predetermined length and wetting diameter.

SUMMARY OF THE INVENTION

The present invention relates to an aqueous leave-on hair conditioning composition which comprises:
a) about 0.01% to about 10.0% of a quaternary ammonium compound that is a cationic conditioning surfactant;
b) 0% to about 10.0% of a silicone compound;
c) about 0.00001% to about 0.05% of a polyoxyethylene polymer; and,
d) about 0.01% to 10% of a non-ionic surfactant
wherein said composition is substantially free of hair hold enhancing agents and wherein the said composition is substantially free of cationic cellulosic resins containing tetra-substituted nitrogen moieties.

The present invention also relates to a method of conditioning hair which comprises contacting said hair with a composition of the invention.

DETAILED DESCRIPTION OF THE INVENTION

As used herein % means weight % unless otherwise indicated. As used herein "narrow conical spray pattern" means a spray pattern that forms, for example, a cone which has an approximately circular base with a radius of about 1 to about 6 inches, more preferably about 2 to about 5 inches; and a height of about 4 to about 16 inches, more preferably about 6 to about 12 inches. "Misty" refers to a spray pattern that does not have clearly defined outer boundaries. "Stream" or "jet" refers to a spray pattern wherein product is disposed within a single straight line. MW/m refers to weight average molecular weight in millions of Daltons. As used herein "substantially free" means less than 0.01%, preferably less than 0.05% and more preferably less than 0.005%. Compositions of the invention may be made by means which are known in the art or which are analogous to those which are known in the art. Ingredients that are included in compositions of the invention are known in the art or may be made by means that are known in the art.

The present invention relates to an aqueous leave-on hair conditioning composition which comprises:
a) about 0.01% to about 10.0% of a quaternary ammonium compound that is a cationic surfactant;
b) 0% to about 10.0% of a silicone compound;
c) about 0.00001% to about 0.05% of a polyoxyethylene polymer; and
d) about 0.01 percent to about 10.0 percent of a non-ionic surfactant
wherein said composition is substantially free of hair hold enhancing agents and wherein said composition is substantially free of cationic cellulosic resins containing tetra-substituted nitrogen moieties.

The present invention also relates to a method of conditioning hair which comprises contacting said hair with a composition of the invention.

More preferably compositions of the present invention may comprise:

a) about 0.1% to about 5.0% of a quaternary ammonium compound that is a cationic conditioning surfactant;
b) 0% to about 5.0% of a silicone compound
c) about 0.0001% to about 0.01% of a polyoxyethylene polymer, and
d) about 0.1% to about 5% of a non-ionic surfactant.

Still more preferably, compositions of the present invention may comprise:
a) about 0.5% to about 2.0% of a quaternary ammonium compound that is a cationic conditioning compound;
b) 0% to about 1.0% of a silicone compound
c) about 0.001% to about 0.006% of a polyoxyethylene polymer, and
d) about 0.5% to about 2% of a non-ionic surfactant.

Compositions of the invention may also comprise long chain fatty alcohols of C8–C24, more preferably C12–C22 and most preferably C14–C20 alkyl hydrocarbon chains.

Compositions of the invention may further comprise buffers, organic acids, organic solvents that are miscible with water surfactants, anti-oxidants, preservatives, colorants, fragrances, and the like.

There is now provided a description of the ingredients which may be included in the compositions of the present invention.

Quaternary Ammonium Compound

The conditioning compositions of the present invention may contain at least a water-soluble or water-dispersible quaternary nitrogen-containing conditioning agent that is also sometimes referred to herein as a cationic surfactant compound or a quaternary ammonium compound. A long chain fatty alcohol is also present in more preferred compositions, and a tertiary amidoamine is additionally present in particularly preferred compositions.

The quaternary nitrogen-containing conditioning agents are preferably present in compositions of the invention at from about 0.01% to about 10% by weight of the composition as an active ingredient. More preferably, the quaternary nitrogen-containing conditioning agent is present at from about 0.1% to about 5%, as an active ingredient and most preferably from about 0.5% to about 2.0% of the composition.

A class of quaternary nitrogen-containing conditioning agents useful herein can contain one quaternary nitrogen atom having (a) two long aliphatic chains and (b) two identical or different short chain alkyl groups having one or two carbon atoms, each bonded to the quaternary nitrogen atom. The two long chains each contain about 12 to about 18 carbon atoms.

Illustrative conditioning agents include distearyldimethylammonium chloride and dilauryidlmethylammonium chloride. These compounds are named Quaternium-5 and Quaternium-47, respectively, in the CTFA Cosmetic Ingredient Dictionary, 2nd ed., 1977, published by the Cosmetic, Toiletry and Fragrance Association, Inc., hereinafter referred to as the CTFA Dictionary.

It is noted that the long aliphatic chain of the before-mentioned conditioning agents need not be solely or primarily of one chain length, that is, the long chain need not be cetyl, myristyl, lauryl or stearyl. Rather, conditioning agents whose long aliphatic chain contains a mixture of lengths can be used. Such conditioning agents are conveniently prepared from naturally occurring materials, such as tallow, coconut oil, soya oil and the like, or from synthetically produced mixtures. Examples of useful conditioning agents having mixed aliphatic chain lengths include dimethyldi(hydrogenated tallow)ammonium chloride and dialkyldimethylammonium chloride wherein each alkyl group is a saturated group consisting primarily of 16 carbon atoms. These quaternary nitrogen-containing conditioning agents are named Quaternium-18 and Quaternium-31, respectively, in the CTFA Dictionary.

Other exemplary conditioning agents are alkyl ester quaternary ammonium compounds. An example of an ester quat is dipalmitoylethyidimonim chloride available as Armocare VGH-70 from Akzo Nobel Inc.

Volatile Silicone Oils and Hydrocarbon Oils

Volatile silicone oils may also be employed in the compositions of the invention. A volatile silicone oil is often described as a volatile polyorganosiloxane, and is a liquid material having a measurable vapor pressure at ambient conditions (about 20 to 25° C.). Typically the vapor pressure of volatile silicones lies in the range of from 1 or 10 Pa to 2 kPa at 25° C. Volatile polyorganosiloxanes can be linear or cyclic or mixtures thereof. Preferred cyclic polysiloxanes include polydimethylsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $1 \times 10^{-5}$ $m^2$/sec (10 centistokes), and particularly above $1 \times 10^{-7}$ m 2/sec (0.1 centistokes). The linear siloxanes normally exhibit a viscosity of below $5 \times 10^{-6}$ $m^2$/sec (5 centistokes). The volatile silicones can also comprise branched linear or cyclic siloxanes such as the aforementioned linear or cyclic siloxanes substituted by one or more pendant —O—Si(CH$_3$)$_3$ groups. Examples of commercially available silicone oils include oils having grade designations 344, 345, 244, 245 and 246, (from Dow Corning Corporation); Silicone 7207 and Silicone 7158 (from Union Carbide Corporation); and SF1202 (from General Electric [US]).

The compositions of the present invention may also comprise volatile hydrocarbon oils having about 10 to about 30 carbon atoms. A preferred volatile hydrocarbon compound is an aliphatic hydrocarbon having about 12 to about 14 carbon atoms, and having a boiling point of about 100° C. to 250° C. Examples of volatile hydrocarbon compounds include, but not limited to, isododecane and isohexadecane, that is, PERMETHYL 99A, PERMETHYL 101A and PERMETHYL 102A, available from Presperse Inc., South Plainfield, N.J. Another exemplary volatile hydrocarbon compound is ISOPAR M (a $C_{13}$–$C_{14}$ isoparaffin available from Exxon Chemical Co., Baytown, Tex.).

Non-Volatile Silicone and Hydrocarbon Oils

The non-volatile oil can comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include, Dow Corning 949 (amodimethicone emulsion with an internal viscosity of about 2000 centistokes), Dow Corning 200 series having a viscosity of at least 50 centistokes and Dow Corning emulsions DC 1766, 1784 and 1786 (dimethiconol emulsions with an internal viscosity of about 1 million centistokes). A mixture of a non-volatile low molecular weight polydimethyl siloxane fluid and a high molecular weight polydimethyl siloxane gum may also be used in the present invention. Silicone gums useful in compositions of the present invention are available from a variety of commercial sources including General Electric Company, Waterford, N.Y. and Dow Corning Corp. Midland, Mich.

The non-volatile silicone oils are preferably present at from 0% to about 10% as an active ingredient. More preferably, the non-volatile silicone conditioning oil are present at from 0% to about 5%, as an active ingredient and most preferably from 0% to 2.0% of the composition.

The compositions of the present invention, in addition, may comprise non-volatile hydrocarbon oils such as mineral oil. Other exemplary non-volatile hydrocarbon compounds that can be incorporated include, but not limited to, a branched 1-decene oligomer, like 1-decene dimer or a poly-decene.

Poly Oxyethylene/Oxypropylene Polymer

The compositions of the present invention comprise from about 0.00001% to about 0.05%, more preferably from about 0.0001% to about 0.01%, and most preferably from about 0.001% to about 0.006% of a polymer of ethylene oxide and/or propylene oxide.

The polymers of the present invention are characterized by the general formula: $HO(CRHCH_2O)_nH$ wherein R is selected from the group consisting of H, methyl, and mixtures thereof. When R is H, these materials are polymers of ethylene oxide, which are also known as polyethylene oxides, polyoxyethylenes, and polyethylene glycols.

When R is methyl, these materials are polymers of propylene oxide, which are also known as polypropylene oxides, polyoxypropylenes, and polypropylene glycols. When R is methyl, it is also understood that various positional isomers of the resulting polymers can exist.

In the above structure, n has an average value of from about 2,000 to about 14,000, preferably from about 5,000 to about 9,000, more preferably from about 6,000 to about 8,000.

Polyethylene glycol polymers useful herein that are especially preferred are PEG-2M wherein R equals H and n has an average value of about 2,000 (PEG-2M is also known as Polyox WSR N-10 from Union Carbide, and as PEG-2,000); PEG-5M wherein R equals H and n has an average value of about 5,000 (PEG-5M is also known as Polyox WSR N-80, from Union Carbide); PEG-7M wherein R equals H and n has an average value of about 7,000 (PEG 7-M is also known as Polyox WSR N-750 from Union Carbide); PEG-9M wherein R equals H and n has an average value of about 9,000 (PEG 9-M is also known as Polyox WSR N-3333 from Union Carbide); PEG-14 M wherein R equals H and n has an average value of about 14,000 (PEG-14M is also known as Polyox WSR N-3000 from Union Carbide); PEG-23 M wherein R equals H and n has an average value of about 23,000 (PEG-23M is also known as Polyox WSR N-12K from Union Carbide); PEG-45 M wherein R equals H and n has an average value of about 45,000 (PEG-45M is also known as Polyox WSR N-60 K from Union Carbide) and PEG-90 M wherein R equals H and n has an average value of about 90,000 (PEG-90M is also known as Polyox WSR-301 from Union Carbide).

Other useful polymers include the polypropylene glycols and mixed polyethylene/polypropylene glycols.

All percentages describing the polymers in this section of the description herein, are by weight of the total composition, unless otherwise specified.

Non-Ionic Surfactant

The compositions of the invention comprise preferably from 0.01 to 10 weight percent, more preferably from 0.1 to 5 weight percent and most preferably from 0.5 to 2.0 wt. % of a non-ionic surfactant or a mixture of non-ionic surfactants.

Non-ionic surfactants that can be incorporated include ethoxylated alcohols, ethoxylated lanolin and castor oils, ethoxylated polysiloxanes, alkyl glucosides, polyoxyethylene/polypropylene glycol ethers, alkanolamides, amine oxides, ethoxylated glycerides, glycol esters, monoglycerides, polyglyceryl esters, carbohydrate derived esters, ethoxylated carboxylic acids, sorbitan esters, all containing hydrocarbon chains in the range of $C_8$–$C_{26}$.

Exemplary classes of non-ionic surfactants include, but are not limited to alkoxylated alcohols and alkoxylated polyol esters and ethers. Exemplary materials useful in this regard include ethoxylated lanolin and ethoxylated sorbitan esters. An exemplary ethoxylated sorbitan ester useful in the compositions of the invention is polyoxyethylene 20 sorbitan monolaurate that has an HLB value of 16.7, available as Tween 20 from ICI Surfactants of Wilmington, Del. HLB is hydrophile-lipophile balance number that is widely used scale to rate surfactants [W. C. Griffin, Journal of Society of Cosmetic Chemists, Vol.5, page 249, 1954]. A given HLB value can be accessed through a single surfactant or any combination of surfactants. The preferred HLB value of the surfactant is in the range of 12 to 24, more preferably 14 to 20 and most preferably 16 to 18.

Solvents

Water is the preferred principal diluent or solvent for the compositions according to the present invention. As such, the compositions according to the present invention may include one or more solvents as additional diluent materials. Generally, the solvent is selected to be miscible with water and innocuous to the skin. Solvents suitable for use herein include $C_1$–$C_{20}$ mono- or polyhydric alcohols and their ethers, glycerine, with monohydric and dihydric alcohols and their ethers preferred. In these compounds, alcoholic residues containing 2 to 10 carbon atoms are preferred. Thus, a particularly preferred group includes ethanol, isopropanol, n-propanol, butanol, propylene glycol, ethylene glycol monoethyl ether, and mixtures thereof.

Propellants

In the present invention, the propellant, if present, is selected from the group consisting of: trichlorofluoromethane, dichlorodifluoromethane, dichlorotetraflouromethane, methyl acetate, dimethyl ether, propane, n-butane, isobutane and mixtures thereof, and like propellants.

Fatty Alcohols and Thickeners

Fatty alcohols and thickeners may be included in compositions of the invention. Long chain fatty alcohols having from about 8 to about 24 carbon atoms, preferably from about 12 to 22 carbon atoms and more preferably from about 14 to 20 carbon atoms in the long fatty chain, can be thickener constituents of compositions of this invention. These alcohols can be used alone, or in admixture with each other. When included in the compositions, the alcohol is preferably present at from about 0.5 to about 10 weight percent of the composition, and more preferably at from about 1 to about 5 weight percent.

Lauryl alcohol, oleyl alcohol, myristyl alcohol, stearyl alcohol, behenyl alcohol and the like, and mixtures thereof are contemplated herein. In addition, mixtures of natural or synthetic fatty alcohols having fatty chain lengths of from about 11 to about 18 carbons are also useful. Several such mixtures are available commercially, and are exemplified by the material containing a mixture of synthetic alcohols with 12 to 15 carbons in the alkyl chain sold under the trademark NEODOL 25 by Shell Chemical Company, and the material containing a mixture of synthetic alcohols with chain lengths of 12 to 16 carbons sold under the trademark ALFOL 1216 Alcohol by Conoco Chemicals.

Thickening agents suitable for use in the compositions herein may also be selected from the group consisting of oleic acid, cetyl alcohol, oleyl alcohol, cetearyl alcohol, stearyl alcohol, synthetic thickeners such as Carbopol, Aculyn and Acrosyl and mixtures thereof. Preferred thickeners for use herein are Aculyn 22 (RTM), steareth-20 methacrylate copolymer; Aculyn 44 (RTM) polyurethane resin and Acusol 830 (RTM), acrylates copolymer that are available from Rohm and Haas, Philadelphia, Pa., USA. Additional thickening agents suitable for use herein include sodium alginate or gum arabic, or cellulose derivatives, such as methyl cellulose or the sodium salt of carboxymethylcellulose or acrylic polymers.

Fatty alcohols of the above discussed carbon chain lengths which are ethoxylated to contain an average of one or two moles of ethylene oxide per mole of fatty alcohol can be used in place of the fatty alcohols themselves. Examples of such useful ethoxylated fatty acids include ethylene glycol cetyl ether, polyoxyethylene (2) stearyl ether, and the like; the exemplary compounds having CTFA Dictionary names of Ceteth-1 and Steareth-2, respectively.

Glycols and Surfactants

The compositions of the invention may further comprise additional components such as glycols or polyols, surfactants, and fatty alcohols. Exemplary glycols include, but are not limited to propylene glycol, butylene glycol, hexylene glycol, and mixtures thereof. An exemplary polyol useful in the compositions is glycerine.

The compositions of the invention may be in the form of a conditioning shampoo, a rinse-off conditioner, a leave-on conditioner or a hair derange. The compositions are preferably in the form of a leave-on conditioner.

Optional Ingredients

The compositions of the present invention can comprise a wide range of optional ingredients. Examples of the functional classes into which these ingredients may fall include: anticaking agents, antioxidants, binders, biological additives, bulking agents, chelating agents, chemical additives, colorants, cosmetic astringents, cosmetic biocides, denaturants, drug astringents, emulsifiers, film formers, fragrance components, humectants, opacifying agents, plasticizers, preservatives, propellants, reducing agents, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, and the like.

Other optional ingredients include organic acids. A non-exclusive list of examples of organic acids which can be used as the proton donating agent are adipic acid, tartaric acid, citric acid, maleic acid, malic acid, succinic acid, glycolic acid, glutaric acid, benzoic acid, malonic acid, salicylic acid, gluconic acid, polyacrylic acid, their salts, and mixtures thereof. A non-exclusive list of examples of mineral acids for use herein is as follows: hydrochloric, phosphoric, sulfuric and mixtures thereof.

Materials which may be employed in the compositions of the invention, are set forth in the table just below.

| Ingredient | Supplier | Chemical Name | Remarks |
|---|---|---|---|
| Citric acid | | | pH modifier |
| Propylene glycol | | | Solvent |
| Polymer JR 30M | Union Carbide | Cationic cellulose | Rheology modifier |
| Polymer WSR N-12K | Union Carbide | Polyethylene glycol, MW 1 million Daltons | Rheology modifier |
| Polymer WSR N-60K | Union Carbide | Polyethylene glycol, MW 2 million Daltons | Rheology modifier |
| Polymer WSR-301 | Union Carbide | Polyethylene glycol, MW 4 million Daltons | Rheology modifier |
| Arquad 2HT | Akzo Nobel | Hydrogenated ditallow diammonium chloride | Cationic conditioning surfactant |
| Tween 20 | ICI | Polysorbate 20, nonionic surfactant | Emulsifier |
| Fragrance | | | |
| Versene 100 | | | Preservative |
| DC 949 | Dow Corning | Amodimethicone emulsion | Conditioning agent |
| Glydant | | | Preservative |
| De-ionized Water | | | Diluent/Carrier |

Method for Preparing the Compositions of the Invention

The following is a method for preparing a composition of the invention.

1. Pre-wet polymer and polymer WSR with propylene glycol
2. Turn on mixer/agitator to moderate speed
3. Add de-ionized water and mix until all polymers are dissolved
4. Add liquid citric acid
5. Add Arquad 2HT and propylene glycol and mix well
6. In a separate beaker, mix polysorbate 20 and fragrance until clear. Add the pre-mix to the main beaker
7. Add silicone emulsion (DC949) and mix well
8. Add preservatives (glydant and versene etc.) and mix well.

The following non-limiting examples of the invention were made.

Formulas 1, 2, 6 and 10 below are comparative examples, and not examples of the invention.

EXAMPLES

Example 1

| Ingredient | Formula 1 wt % | Formula 2 wt % | Formula 3 Wt % | Formula 4 wt % | Formula 5 wt % |
|---|---|---|---|---|---|
| Citric acid | 0.08 | 0.08 | 0.08 | 0.08 | 0.08 |
| Propylene glycol | 0.7 | 0.7 | 0.7 | 0.7 | 0.7 |
| Polymer JR 30M | — | 0.075 | — | — | — |
| Polymer WSR N-12 K | — | — | .005 | — | — |
| Polymer WSR N-60 K | — | — | — | 0.005 | — |
| Polymer WSR 301 | — | — | — | — | 0.005 |
| Arquad 2HT | 1.4 | 1.4 | 1.4 | 1.4 | 1.4 |
| Polysorbate 20 | 0.7 | 0.7 | 0.7 | 0.7 | 0.7 |
| Fragrance | 0.2 | 0.2 | 0.2 | 0.2 | 0.2 |
| Versene 100 | 0.2 | 0.2 | 0.2 | 0.2 | 0.2 |
| DC 949 | 0.4 | 0.4 | 0.4 | 0.4 | 0.4 |
| Glydant | | | | | |
| Water | to 100 | to 100 | To 100 | to 100 | to 100 |
| Spray Pattern | Misty | Conical | Conical | conical | conical |
| Visual appearance after 15 hours | Stable | Unstable | Stable | stable | stable |

Example 1 shows that Formula 1 that does not contain a polymer produces a misty spray, while Formulas 2 to 5 that contain a polymer produce the desirable conical spray. However, cationic cellulose polymer (Polymer JR 30M) renders the formulation unstable (visually a clear interface between the top and the bottom layer of solids is observed) whereas polyethylene glycol polymers (Polymer WSR N-12K, N-60K and 301) produce a stable (no clear interface between the top and the bottom layers is seen) spray.

Example 2

| Ingredient | Formula 1 Wt % | Formula 5 wt % | Formula 6 Wt % | Formula 7 wt % |
|---|---|---|---|---|
| Citric acid | 0.08 | 0.08 | 0.08 | 0.08 |
| Propylene glycol | 0.7 | 0.7 | 0.7 | 0.7 |
| Polymer WSR 301 | — | 0.005 | — | 0.005 |
| Arquad 2HT | 1.4 | 1.4 | 1.4 | 1.4 |
| Polysorbate 20 | 0.7 | 0.7 | 1.4 | 1.4 |
| Fragrance | 0.2 | 0.2 | 0.2 | 0.2 |
| Versene 100 | 0.2 | 0.2 | 0.2 | 0.2 |
| DC 949 | 0.4 | 0.4 | 0.4 | 0.4 |
| Glydant | | | | |
| Water | to 100 | to 100 | To 100 | To 100 |
| Spray Pattern | Misty | Conical | Misty | Conical |
| Total non-volatile solids ratio, w/w (top/bottom), 2 weeks @ room temperature | 0.26 | 0.43 | 0.27 | 0.14 |

In the set of experiments exemplified by the compositions in Example 2, stability was determined quantitatively as follows: The samples were let stand undisturbed at room temperature for 2 weeks. After two weeks a clear interface was seen between the top and the bottom layers. The top layer was pipetted out and the non-volatile content of the two layers determined by evaporating the volatile portion. The non-volatile solids comprise of citric acid, Polymer WSR-301, Arquad 2HT, Polysorbate 20 and DC 949. Stability is defined as the ratio of non-volatile solids between the top and bottom layers.

This example shows that highest stability (as indicated by lower number of the ratio of total non-volatile solids ratio between top and bottom layer) is obtained with Formula 7 which contains a combination of 1.4% polysorbate 20 (non-ionic surfactant) and 0.005 wt % Polymer WSR 301 (non-ionic polymer).

Example 3

| Ingredient | Formula 2 wt % | Formula 8 wt % | Formula 9 Wt % | Formula 5 wt % | Formula 10 wt % |
|---|---|---|---|---|---|
| Citric acid | 0.08 | 0.08 | 0.08 | 0.08 | 0.08 |
| Propylene glycol | 0.7 | 0.7 | 0.7 | 0.7 | 0.7 |
| Polymer JR 30M | 0.075 | | | | |
| Polymer WSR 301 | — | 0.0001 | 0.001 | 0.005 | 0.01 |
| Arquad 2HT | 1.4 | 1.4 | 1.4 | 1.4 | 1.4 |
| Polysorbate 20 | 0.7 | 0.7 | 0.7 | 0.7 | 0.7 |
| Fragrance | 0.2 | 0.2 | 0.2 | 0.2 | 0.2 |
| Versene 100 | 0.2 | 0.2 | 0.2 | 0.2 | 0.2 |
| DC 949 | 0.4 | 0.4 | 0.4 | 0.4 | 0.4 |
| Glydant | | | | | |
| Water | to 100 | to 100 | To 100 | to 100 | to 100 |
| Spray Pattern | Conical | Conical | Conical | Conical | Jet |

Example 3 shows at increasing Polymer WSR 301 from 0.005 to 0.01 weight percent results in transformation of spray pattern from Conical to Jet.

Packages which Contain Compositions of the Invention

For maximum convenience to the consumer, the package which contains the composition of the invention is preferably a dispensing package such as a spray dispenser or a foam dispenser. When the composition of the invention is in the form of a leave-on conditioner or a hair detangler, it is preferably contained in a spray dispenser package. Such packages contain a piston pump by which the composition is dispensed in the form of a spray. As such, leave-on conditioners or hair detanglers comprising the compositions of the invention should have relatively low viscosity to permit the compositions to be readily dispensed via such pump dispensers.

How to Use Compositions of the Invention

The compositions of the invention are especially useful in hair detangling range of products, where they facilitate the detailing of tangled hair by reducing the force required to comb tangled hair as discussed hereinabove. The compositions may be used either when the hair is wet or dry. If the hair is wet, it is preferable that excess water be squeezed from the hair, and that the compositions of the invention be uniformly applied to the hair, as for example, from a spray dispenser. The composition may then be worked into the hair and the hair may then be combed or brushed. Alternatively, for use on dry hair, the compositions should be applied to the hair until the hair becomes damp and then the hair is combed or brushed.

We claim:

1. A sprayable aqueous leave-on hair conditioning composition which comprises:
   a.) about 0.01 percent to about 10.0 percent of a quaternary ammonium compound that is dicetyldimethylammonium chloride, distearyl dimethylammonium chloride, ditallow dimethyl ammonium chloride or mixtures thereof;
   b.) about 0.0 percent to about 10.0 percent of a silicone oil;

c.) about 0.0001 to about 0.01% of a polyoxyethylene polymer; and
d.) about 0.01 to about 10% of a non-ionic surfactant,
wherein said composition is substantially free of hair hold enhancing agents and which is substantially free of cationic cellulosic resins containing tetra-substituted nitrogen moieties.

2. A sprayable aqueous leave-on hair conditioning composition which comprises
   a.) about 0.1 percent to about 5.0 percent of a quaternary ammonium compound having (i) two long aliphatic chains and (ii) two tical or different short alkyl groups having one or two carbon atoms, each bonded to the quaternary nitrogen atom, wherein the two long chains each contain about 12 to about 18 carbon atoms;
   b.) about 0.0 percent to about 5.0 percent of a silicone oil;
   c.) about 0.001 to about 0.01% of a polyoxyethylene polymer; and
   d.) about 0.1 to about 5.0% of a non-ionic surfactant, wherein said composition is substantially free of hair hold enhancing agents and which is substantially free of cationic cellulosic resins containing tetra-substituted nitrogen moieties.

3. A composition according to claim 1 which comprises
   a.) about 0.5 percent to about 2.0 percent of a quaternary ammonium compound;
   b.) about 0 percent to about 1.0 percent of a silicone oil;
   c.) about 0.001 to about 0.006% of a polyoxyethylene polymer, and
   d.) about 0.5 to about 2.0% of a non-ionic surfactant.

4. An aqueous leave-on hair conditioning composition which comprises:
   a.) about 0.01 percent to about 10.0 percent of dipalmitoylethyldimonium chloride;
   b.) about 0.0 percent to about 10.0 percent of a silicone oil;
   c.) about 0.0001 to about 0.01% of a poyoxyethylene polymer; and
   d.) about 0.1 to about 10% of a non-ionic surfactant,
wherein said composition is substantially free of hair hold enhancing agents and which is substantially free of cationic cellulosic resins containing tetra-substituted nitrogen moieties.

5. A composition according to claim 1, wherein the silicone oil is amodimethicone of viscosity of about 2000 centistokes in the form of an emulsion.

6. A composition according to claim 1, wherein the silicone oil is dimethiconol of about 1 million centistokes in the form of an emulsion.

7. A composition in accordance with claim 1, wherein polyoxyethylene oxide polymer has a weight average molecular weight of from about 0.1 to about 8 MW/m.

8. A composition in accordance with claim 1, wherein polyoxyethylene oxide polymer is more preferably about 0.2 to about 6 MW/m.

9. A composition in accordance with claim 1 wherein polyoxyethylene oxide polymer is most preferably about 0.3 to about 4 MW/m.

10. A composition according to claim 1, wherein the non-ionic surfactant has a HLB value between 12 to 24.

11. A composition according to claim 1, wherein the non-ionic surfactant has a HLB value between 14 to 20.

12. A composition according to claim 1, wherein the non-ionic surfactant has a HLB value between 16 to 18.

13. A composition according to claim 1 wherein the non-ionic surfactant is poly(oxyethylene) 20 sorbitan monolaurate.

14. A method for treating hair that comprises contacting said hair with a composition according to claim 1.

* * * * *